US006772002B2

(12) United States Patent
Schmidt et al.

(10) Patent No.: US 6,772,002 B2
(45) Date of Patent: Aug. 3, 2004

(54) DEVICE AND METHOD FOR NAVIGATION

(75) Inventors: Robert Schmidt, Poing (DE); Akos Dombay, Höhenkirchen (DE); Andreas Hartlep, München (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 241 days.

(21) Appl. No.: 09/954,476

(22) Filed: Sep. 12, 2001

(65) Prior Publication Data
US 2002/0087062 A1 Jul. 4, 2002

(30) Foreign Application Priority Data
Nov. 24, 2000 (EP) ............................................. 00125274

(51) Int. Cl.[7] .................................................. A61B 5/05
(52) U.S. Cl. ...................... 600/429; 600/407; 600/417; 600/424
(58) Field of Search ................................ 600/407–482

(56) References Cited
U.S. PATENT DOCUMENTS 5,588,430 A  12/1996  Bova et al.
5,891,034 A   4/1999  Bucholz
5,999,840 A  12/1999  Grimson et al.
6,122,541 A   9/2000  Cosman et al.

FOREIGN PATENT DOCUMENTS

DE  3931531  4/1990

Primary Examiner—Angela D. Sykes
Assistant Examiner—William C. Jung
(74) Attorney, Agent, or Firm—Renner, Otto, Boisselle & Sklar, LLP

(57) ABSTRACT

The present invention relates to a method for determining the position of at least one object in a navigation system of co-ordinates, wherein: reference points and/or markers (4) are connected in a defined positional relationship to the object; the position of the object is detected in relation to a detection system of co-ordinates; the position of the reference points (4) is detected in relation to the detection system of co-ordinates; the position of the reference points is detected in relation to a navigation system of co-ordinates; and the position of the object is determined in the navigation system of co-ordinates, from the position of the at least one reference point (4) in the detection system of co-ordinates; as well as to a device for determining the position of an object in a navigation system of co-ordinates.

17 Claims, 2 Drawing Sheets

DEVICE AND METHOD FOR NAVIGATION

Figure 1:
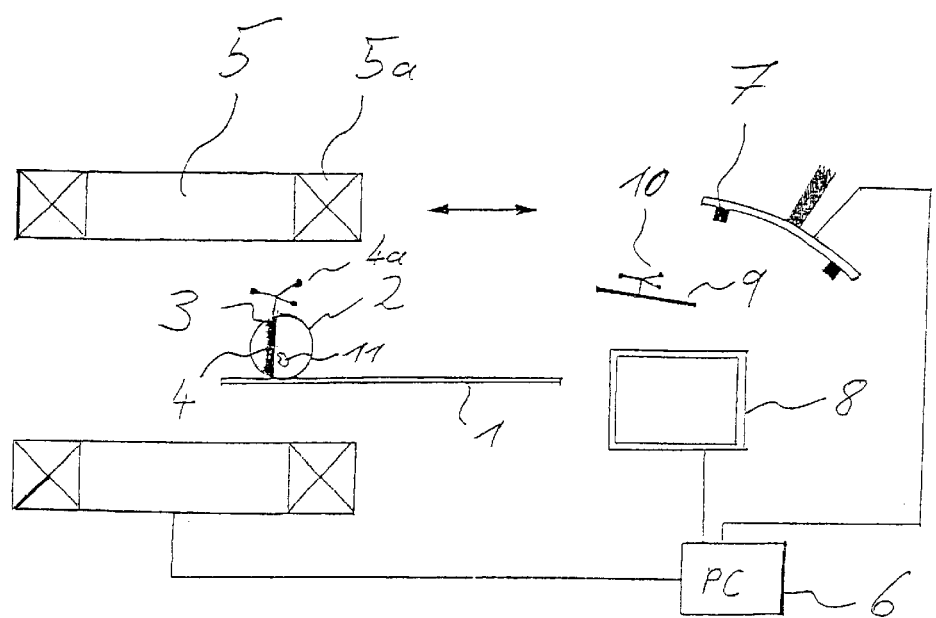

The present invention relates to a method and a device for navigation, in particular in intra-operative data capture. In general, the invention relates to a method and a device for localising a specified object, located for example in an external body such as for example a tumour, in a defined system of co-ordinates, such that it is possible to detect the spatial location of the tumour or of another area of interest exactly, continually and dynamically at any time, for example when a person in whom a tumour has been localised moves.

A method and a device for calibrating a navigation system with respect to image data from a magnetic resonance device for positioning a patient in a magnetic resonance device is known from DE 198 05 112 A1. In this respect, positions of at least three markers arranged in an image volume of a magnetic resonance device are determined in a first system of co-ordinates using a navigation system and in a second system of co-ordinates by means of magnetic resonance, whereby the position and orientation of the two co-ordinate systems relative to one another are determined from the positions of the markers in the two systems of co-ordinates, such that co-ordinate data from the first system of co-ordinates can be transformed into co-ordinate data of the second system of co-ordinates on the basis of a co-ordinate transformation matrix determined in this way. This method enables a patient to be positioned as exactly as possible in a magnetic resonance device, such that a specified area of the patient in which, for example, a tumour is suspected can be marked with an indicator instrument in order to produce a cross-sectional image in a plane given by the indicator instrument. If the patient is taken out of the magnetic resonance device again after imaging, then only the data of specified cross-sectional images are known, however an object of interest cannot be localised spatially, i.e. after the person has been taken out of the magnetic resonance device, the exact current spatial position of objects of interest in a person cannot be directly or precisely determined.

A method for comparing images recorded over a specified period of time with one another by means of nuclear spin resonance is known from the article "Motion Compensation by Gradient Adjustment" by H. Eviatar et al., Institute for Biodiagnostics, National Research Council Canada, Winnipeg, Manitoba, Canada; ISMRM Procedures 1997. To this end, reference elements are firmly attached to a head, said elements determining a recording area, such that it can be determined, in relation to these reference elements and independent of possible other positioning of a head to be examined relative to a magnet, whether certain areas of for example the brain have shifted due to relative movements. According to this method as well, it is not possible to continuously directly determine the position of an area of interest if a person to be examined has been taken out of the nuclear spin resonance device again.

It is the object of the present invention to propose a method and a device for determining the position of an object, such as for example a tumour in the cerebral tissue, which enable the relative position of the object of interest to be continually and precisely determined in a reference system of co-ordinates. In particular, a method and a device are to be proposed with which intra-operative images of a body containing the object can be taken, wherein the exact position of the object or of areas of interest or areas recorded with respect to a system of co-ordinates can be continually determined even if the body, for example a person to be examined, is taken out of, for example, a nuclear spin resonance or computer tomography apparatus, enabling precise navigation to be provided as a support in examining or treating a person.

This object is solved by a method and a device comprising the features of the independent claims. Advantageous embodiments arise from the sub-claims.

In the method in accordance with the invention for determining the position of an object in a navigation system of co-ordinates, wherein in general one or more geometric points can also be seen as an object, one or more reference points which are also designated as markers and which exhibit a specific reaction or reflex behaviour with respect to a signal detecting device employed are connected to the object in a defined positional relationship. It is not necessary for the reference points or markers to be directly arranged on the object, which is not possible when the object is surrounded by an external body. In general, firmly attaching or fixing markers in a positional relationship which is as stable as possible, i.e. not easily shifted by the effect of external forces, for example to the external body, is sufficient. For example, one or more markers can be provided on a head to be examined via a special clamp arranged on the head. Such clamps are widely known and are designated as skull clamps or Mayarea™ clamps. In such an application, the markers can either be integrated into the skull clamp or arranged, for example attached, at a defined position in a defined positional relationship. These markers, firmly connected to the object or in a firmly defined positional relationship to it, can be used to determine the position of, for example, the external body in a detection system of co-ordinates, wherein the position of or changes in the position of the object of interest lying in the external body, for example a cerebral area shifting due to a change in the pressure ratios after the cranium has been opened up, also known as "brainshift", are also detected in the detection system of co-ordinates. To this end, the position of the object is first determined and/or recorded with reference to the detection system of co-ordinates, i.e. for example with respect to a system of co-ordinates of a nuclear spin resonance device or of the detection area of an image recording apparatus, wherein the position of the reference points or markers is also determined with respect to this detection system of co-ordinates. The position of the markers can be detected before, after or at the same time as detecting the position of the object. Thus, a relative positional relationship between the detected object and the detected reference points or markers can be determined, such that the position of the object is clearly defined when the co-ordinates of the reference points or markers are known. The position of the markers is then determined in relation to a navigation system of co-ordinates, such that the markers can be exactly spatially localised, i.e. the co-ordinates of the marker or markers are determined in relation to a system of co-ordinates for navigation. Since the relative positional relationship between the object and the markers has been determined beforehand, for example in a nuclear spin tomograph, the absolute position of the object can be determined spatially using the navigation co-ordinates of the markers. In this way, the position of the object can be continuously determined, i.e. where the object of interest, for example a tumour or other area of tissue, is spatially located in relation to a navigation system of co-ordinates can be continually determined even, for example, after a person has been taken out of a nuclear spin tomograph, since the navigation system of co-ordinates is in a fixed and known relationship to the object to be measured. This can be advantageous in examination or treatment, since for example an instrument for treatment can be moved to a desired position relative to the object while simultaneously detecting the spatial position of this instrument for treatment. In accordance with the invention, the position of the object of interest is thus not "lost", as is the case in the method in accordance with the prior art described above, but can for example instead be continually determined.

In the sense of the invention, however, it is not necessary to use the same reference points or markers in order to determine the positional relationship between the markers and the object in a first step, and to determine the position of the object from the recorded position of the markers in a second step. Various different markers or reference points may also be used, for example for a nuclear spin resonance image and for IR navigation, when for example these are in a defined, known positional relationship to each other. It is of course also possible to use the same markers or to combine or integrate into each other markers with specific properties favourable to the respective detection method.

In accordance with the invention, it is consequently possible to continually detect the exact position of an object of interest in relation to a navigation system of co-ordinates, such that the exact position of the object can be determined even when the object or an external body, for example a person, moves, i.e. said object can be tracked. It is, however, not necessary to continually determine the position, such that intermittent or discrete-time methods can also be used to determine the position of the object at specified points in time, if continual detection is not necessary.

In detecting the object in a suitable device, an anatomical image is advantageously taken first, for example a rough detection or survey scan, i.e. a resolution of a larger detected area (FOV, Area of View) can for example be below the desired resolution for obtaining a required image or an optimum sequence of images. Using such an overview scan or localiser, it is possible to adjust the focusing of the detection device to a desired smaller area, by hand or automatically, for example on the basis of a sequence of images of a larger area taken initially in for example relatively low resolution, such that images from this desired area can be taken, after being focussed using a second imaging sequence or spectroscopy, in for example a higher resolution, or other functional information. Thus, for example, a second, more detailed scanning procedure for an area of interest can be carried out by means of the navigation system of co-ordinates and the position of the markers in relation to the detection system of co-ordinates, even for example from outside the magnets, by automatically focussing on an area specified by the markers. In this way, it is also possible, if necessary, to automatically focus on an area of interest, for example for a more detailed second image, using image-assessing or spectroscopic methods.

In an advantageous embodiment, an area can be determined in the navigation system of co-ordinates in relation to the object, for example by a person performing the treatment, who marks by means of an indicator instrument in the navigation system of co-ordinates, within which data, in particular image data, are detected in the detection system of co-ordinates. If, for example, a patient has been taken out of a nuclear spin tomograph or other suitable imaging device, and if for example the location of a tumour localised in the patient is determined in the navigation system of co-ordinates, then for example by means of an indicator instrument whose position is also determined in the navigation system of co-ordinates, a specific area in the person can be identified which, for example, contains the tumour, such that when the patient is re-inserted into, for example, a nuclear spin tomograph, said area determined in the navigation system of co-ordinates can be focussed on automatically. Thus, an area of interest can be focussed on or adjusted to as desired, on the basis of the position of the markers firmly connected to the object of interest and the area defined in the navigation system of co-ordinates, such that an imaging method can supply data with respect to the area thus specified.

An imaging method, in particular a nuclear spin resonance, ultrasonic or a computer tomography method, is preferably used to determine the spatial location or position or to orientate the object in a detection system of co-ordinates or relative to markers. However, it is possible in general to use any other method which enables the position of an object, which may be arranged in a larger, external object surrounding it, together with the position of one or more reference points or markers to be determined. Suitable methods for determining the position of one or more markers in a navigation system of co-ordinates can, for example, use infrared light, such that for example IR reflecting markers are detected by IR cameras. It is however also possible to use electromagnetic methods or methods based on ultrasound or radio. In general, any method may be used which enables the exact position or one or more points to be determined in relation to a fixed system of co-ordinates.

It is advantageous to use a co-ordinate transformation method to convert the positional data of the object of the markers obtained in the detection system of co-ordinates to the navigation system of co-ordinates. In this respect, reference is made to the teaching in DE 198 05 112 A1, whose disclosure with respect to determining a transformation matrix—in that case only for positioning in a nuclear spin resonance method—is adopted in this description for general application in accordance with the invention of transforming co-ordinates.

Advantageously, the position of at least one other instrument is also detected by at least one detecting device for determining the location in the detection or navigation system of co-ordinates, such as for example the position of a scalpel on the basis of the markers attached to it, such that the positional relationship between the object and the instrument can be determined and possibly visualised, in order for example to automatically position or guide an instrument or in order to provide information regarding the relative positional relationship of the instrument and the object through suitable visual representation of a person, in order to be able to use the instrument as precisely, i.e. exactly positioned, as possible.

The device in accordance with the invention for determining the position of an object or a point in a navigation system of co-ordinates comprises a device for securely, i.e. in a fixed positional relationship, fixing reference points or markers to the object or to a body surrounding the object. Furthermore, a device for recording the position of the object, together with the position of the reference points or markers, is provided in a detection system of co-ordinates. In accordance with the invention, a device for recording the position of the marker(s) or reference points is provided in a navigation system of co-ordinates, wherein the detection devices for determining the position in the detection system of co-ordinates and for determining the position in the navigation system of co-ordinates can be based on various physical principles. Using a data processing device, the position of the object in the navigation system of co-ordinates can be determined from the detected position of the reference point or points in the navigation system of co-ordinates and the relative positional relationship between the object and the marker determined in the detection system of co-ordinates. The device in accordance with the invention works substantially according to the method described above, such that reference is made to this in this respect.

The detection device for determination the position of a reference point or marker in the navigation system of co-ordinates is advantageously arranged outside of the detection device for determining the position of the object and the markers in the detection system of co-ordinates. Infrared cameras for example are thus arranged outside of a nuclear spin tomograph, in order to be able to determine the spatial position of an object of interest outside of the nuclear spin tomograph, after carrying out nuclear spin tomography. However, it is also conceivable to construct the detection device which serves to detect the position in the navigation system of co-ordinates integrally with the device which serves to detect the position in the detection system of co-ordinates, i.e. for example, to integrate one or more infrared cameras into a nuclear spin tomograph.

A skull clamp is preferably used as the device for securely attaching reference points or markers to an object of interest, wherein the markers can either be firmly arranged on the skull clamp and/or integrated into it, or can be attached to it. Since it is possible in accordance with the invention to use detection devices based on two different physical principles for the respective systems of co-ordinates, the individual markers can also be provided separate from one another, i.e. for example, a first type of marker is integrated into the skull clamp while a second type of marker is constructed to be attached. However, all markers can also be integrated, or constructed to be attached. In principle, it is also possible to integrate markers for different detection systems to be integrated into one another, i.e. for example, arranging suitable spool elements or coatings around substances which can be detected by magnetic resonance. As a further arrangement of the invention, it is also possible to provide IR reflecting elements on substances which can be detected by magnetic resonance.

Although the invention was described above using an example based on a skull clamp, other devices can also be provided on an object of interest or object to be examined, these devices being provided with suitable markers, such as for example tracks for examining a bone or cartilage structure, or similar apparatus, insofar as these are securely arranged, i.e. placed in a defined positional relationship to the object of interest.

Preferably, at least two markers are provided for each detection device, wherein three or even four or more markers are advantageously used, which are advantageously not all in one plane, in order to enable clear spatial allocation. These markers can all be constructed the same, i.e. can exhibit the same shape and reflection or absorption properties, according to the type of detection technique used. Furthermore, it is also possible to use differently constructed markers, such that it can be recognised, for example on the basis of size, degree of reflection, geometry or other distinguishing features, which specific marker out of a group of a number of markers in a detection procedure was recorded.

Preferably a display device is provided which can represent the position of the object spatially or the location in the navigation system of co-ordinates, possibly in relation to one or more instruments whose position has possibly been likewise detected by means of suitable markers. For example, the possibility or precision of using such an instrument can be improved by representing the relative positional relationship between the object and an instrument in one or more observation planes and/or in a three-dimensional representation.

A device for performing computer tomography or a nuclear spin resonance method is preferably used as a detection device for determining the position of the object and of suitable markers in a detection system of co-ordinates. In general however, as described above, other devices can be used which enable the position of objects to be determined which may not be freely accessible, i.e. which are surrounded by material or tissue.

The device for detecting the position of a reference point or marker in the navigation system of co-ordinates can be one or more infrared cameras, possibly together with suitable infrared lamps, arrangements of transmitters and receivers for determining the position via radio, loudspeaker and/or microphones for performing position determining methods based on sound, or another suitable device, which enable the position of one or more points to be determined as exactly as possible in a system of co-ordinates.

Advantageously, at least one of the detection devices is designed to be movable, i.e. for example, the nuclear spin tomograph can be shifted over a patient, in order to be able to operate intra-operative imaging, possibly after performing a scout view. It is also possible, for example, to provide movable infrared cameras to determine the position in the navigation system of co-ordinates.

Figure 2:
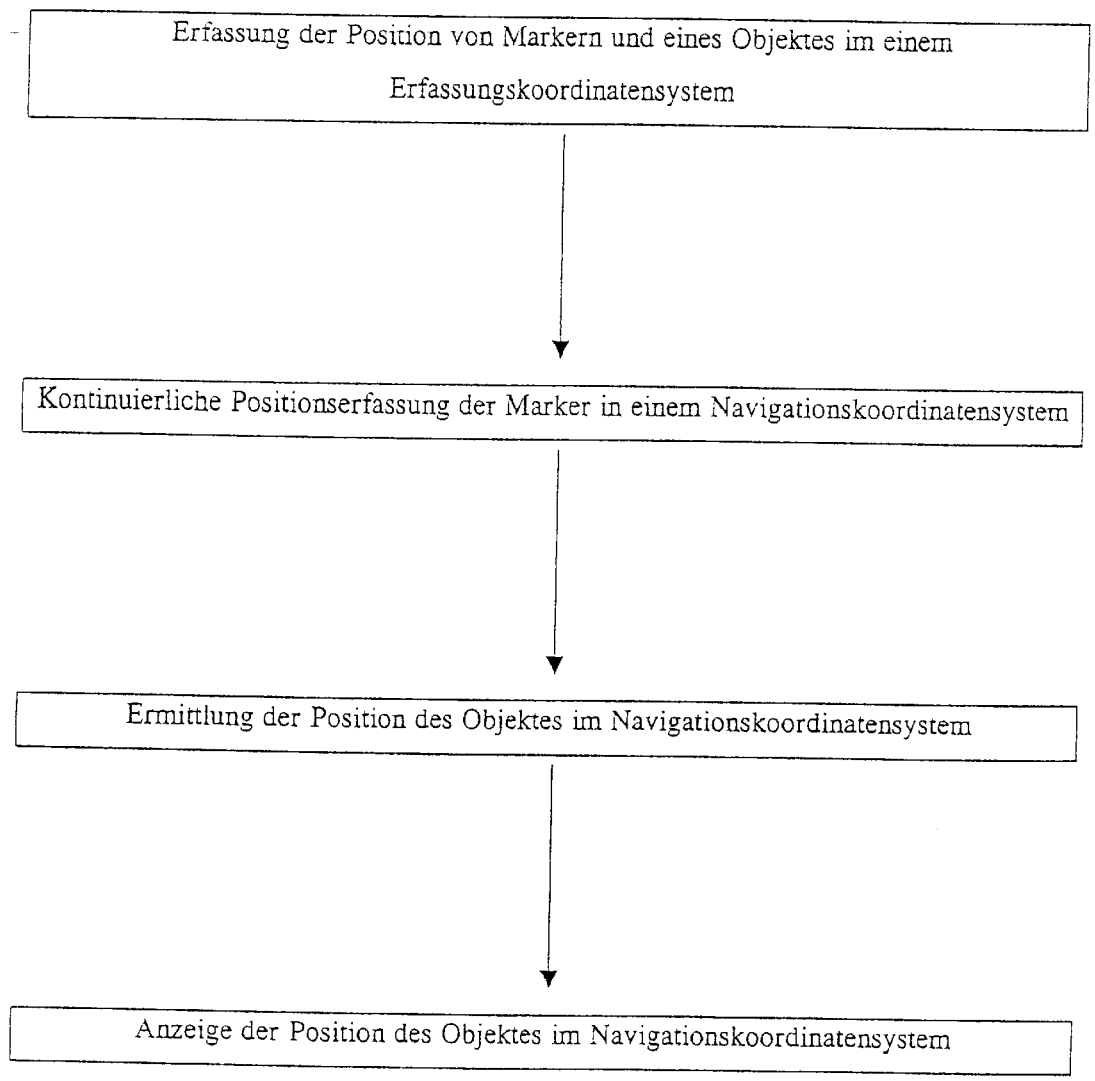

The invention will now be described for a specific embodiment by way of the figures, which show:

FIG. 1 a schematic representation of a device in accordance with the invention; and FIG. 2 a general flow diagram of the method in accordance with the invention.

FIG. 1 shows, in diagram form, a support layer 1 on which an object 2 to be examined, for example the head of a patient, lies, to which a skull clamp 3 is fixed which comprises a number of integrated markers 4 and attachable markers 4a, which in their internal structure comprise a substance which is clearly visible in a nuclear spin resonance method, wherein the markers 4a are provided with a coating which is clearly visible to infrared cameras and are in a fixed and/or restorable relation to the integrated markers 4. The support layer 1 can be inserted into a nuclear spin resonance device 5 using suitable windings 5a, or the nuclear spin resonance device can be moved over the support layer 1 in order to take pre-operative or intra-operative images. The positional data thus detected, for example of a tumour 11 located within the head 2, are transmitted together with the positional data of the markers 4 to a computer 6 which can determine the relative positional relationship in a detection system of co-ordinates from the positions of the markers 4 and the position of the object 11.

When the nuclear spin resonance method is ended, the position of the markers 4a is detected in a navigation system of co-ordinates by infrared cameras 7, wherein the positional data are likewise forwarded to a computer 6. By means of the relative positional data obtained from the nuclear spin tomograph 5, the computer 6 can continually determine the position of the markers 4a, and therefore of the skull clamp 3 or the object 2, using the positional data coming from the infrared cameras 7 to determine the spatial position of the object 11 situated in the body 2 in relation to a navigation system of co-ordinates. The location of the body 2 or of the object 11 arranged in the body 2, such as for example a tumour, can be displayed in relation to a navigation system of co-ordinates three-dimensionally on a screen 8 and/or in various 2D observation planes. In addition, the position of an instrument 9 together with the markers 10 attached to it, which are likewise detected by the infrared cameras 7, are displayed on the screen 8, in order to enable an instrument 9 to be positioned as exactly as possible in relation to the object 11, for example a scalpel to be guided as exactly as possible to a brain tumour.

If, as is possible, changes occur in the position of the object 11 situated in body 2 due to interventions or changes to the body 2, then a further data capture can be performed intra-operatively to determine the current relative position by means of the nuclear spin tomograph 5, so compensating for the changes in the position of the object 11.

FIG. 2 shows in general the principle of the method in accordance with the invention, wherein in a first step, an object together with one of a number of markers is pre-operatively or intra-operatively positioned in a detection system of co-ordinates, within for example the nuclear spin tomograph 5 shown in FIG. 1. After the data capture in, for example, the nuclear spin tomograph is finished, the position of the markers 4a is continually detected in a navigation system of co-ordinates by means of the infrared cameras 7, wherein the position of the object in the navigation system of co-ordinates can be continuously determined from these data, taking into account the relative positional relationship between the object and the markers, previously determined in the detection system of co-ordinates, so that it is possible to continually display the current position of the object in the navigation system of co-ordinates.

If there exists the possibility of a change in the positional relationship between the object and the markers due to interventions or changes to the body 2, then a nuclear spin resonance image can be taken intra-operatively, to exactly obtain the new relative positional relationship between the object and the markers 4, this enabling the accuracy in determining the position of the object to be improved.

What is claimed is:

1. A method for determining the position of at least one object in a navigation system of coordinates, said method comprising the steps of:
    a) fixing at least one reference marker in relation to said object in a defined positional relationship;
    b) using a detection system to detect the said position of said object in a detection system of coordinates;
    c) detecting the position of said at least one reference marker in relation to said detection system of coordinates;
    d) using a navigation system to detect the position of said at least one reference marker in a navigation system of coordinates; and
    e) determining the position of said object in said navigation system of coordinates from the detected position of said at least one reference marker in said navigation system of coordinates and from the detected position of said object relative to said at least one reference marker, as determined in steps b) and c).

2. The method as set forth in claim 1, wherein said position of said object is continuously in said navigation system of coordinates is continuously determined by said navigation system.

3. The method as set forth in claim 1, wherein anatomical image data are detected, before the position of said object and/or of said at least one reference marker is detected by said detection system in said detection system of coordinates in a desired image resolution.

4. The method as set forth in claim 1, wherein an area is specified in said navigation system of co-ordinates in relation to said object, within which area data are detected by said detection system in said detection system of coordinates.

5. The method as set forth in claim 1, wherein said position is detected by said detection system in said detection system of coordinates by using an imaging method.

6. The method as set forth in claim 1, wherein said position is detected by said navigation system in said navigation system of coordinates by using infrared, sound, ultrasonic or electromagnetic, or radio methods.

7. The method as set forth claim 1, wherein a co-ordinate transformation matrix is determined and used to convert detection coordinates into navigation coordinates.

8. The method as set forth in claim 1, wherein the position of further reference markers, and/or at least one instrument, is detected by said detection and/or said navigation system.

9. A device for determining the position of at least one object in a navigation system of coordinates, comprising:
    a) a fixing device which may be arranged in a defined positional relationship on the object;
    b) a detection system for detecting the relative position of said object and of at least one reference marker fixed to said fixing device in a defined positional relationship to said object, in a detection system of coordinates;
    c) a navigation system for detecting the position of said at least one reference marker in a navigation system of coordinates; and
    d) a data processing device for determining said position of said object in said navigation system of coordinates from the detected position of said object relative to said at least one reference marker in said detection system of coordinates and from the detected position of said at least one reference marker in said navigation system of coordinates.

10. The device as set forth in claim 9, wherein said navigation system is separate from said detection system.

11. The device as set forth in claim 9, wherein said at least one reference marker is detachably secured to said fixing device.

12. The device as set forth in claim 9, wherein said at least one reference marker contains a substance which is detectable in a magnetic resonance method and/or in a computer tomography method, and/or comprises a coating which is clearly reflected or visible in a specified spectral range.

13. The device as set forth in claim 9, wherein at least two said reference markers are provided on said fixing device.

14. The device as set forth in claim 13, wherein all said reference markers are constructed the same.

15. The device as set forth in claim 9, wherein a display device is provided for displaying the detected position of said object in said navigation system of coordinates.

16. The device as set forth in claim 9, wherein said detection system includes a device for for performing a nuclear spin resonance procedure, or a computer tomography procedure, and said navigation system includes a device for the detecting light, radio signals or sonic signals.

17. The device as set forth in claim 9, wherein at least one of said navigation system and said detection system is movable.

* * * * *